US006344056B1

(12) United States Patent
Dehdashtian (10) Patent No.: US 6,344,056 B1
(45) Date of Patent: Feb. 5, 2002

(54) VASCULAR GRAFTS FOR BRIDGING A VESSEL SIDE BRANCH

(75) Inventor: Mark Dehdashtian, Costa Mesa, CA (US)

(73) Assignee: Edwards Lifesciences Corp., Irvine, CA (US)

( * ) Notice: Subject to any disclaimer, the term of this patent is extended or adjusted under 35 U.S.C. 154(b) by 0 days.

(21) Appl. No.: 09/473,618

(22) Filed: Dec. 29, 1999

(51) Int. Cl.$^7$ .................................................. A61F 2/06
(52) U.S. Cl. ...................................................... 623/1.35
(58) Field of Search ............................. 623/1.23, 1.27, 623/1.32, 1.35, 1.36, 1.15

(56) References Cited

U.S. PATENT DOCUMENTS

| | | |
|---|---|---|
| 4,149,911 A | 4/1979 | Clabburm |
| 4,225,979 A | 10/1980 | Rey et al. |
| 4,306,318 A | 12/1981 | Mano et al. |
| 4,512,338 A | 4/1985 | Balko et al. |
| 4,553,545 A | 11/1985 | Maass et al. |
| 4,617,932 A | 10/1986 | Kornberg |
| 4,649,922 A | 3/1987 | Wiktor |
| 4,665,906 A | 5/1987 | Jervis |
| 4,665,918 A | 5/1987 | Garza et al. |
| 4,681,110 A | 7/1987 | Wiktor |
| 4,728,328 A | 3/1988 | Hughes et al. |
| 4,729,766 A | 3/1988 | Bergentz et al. |
| 4,732,152 A | 3/1988 | Wallsten et al. |
| 4,762,128 A | 8/1988 | Rosenbluth |
| 4,772,264 A | 9/1988 | Cragg |
| 4,800,882 A | 1/1989 | Gianturco |

(List continued on next page.)

FOREIGN PATENT DOCUMENTS

| | | |
|---|---|---|
| DE | 1766921 | 9/1970 |
| EP | 0177300 | 3/1986 |
| EP | 0335341 | 10/1989 |
| EP | 0421729 | 4/1991 |
| EP | 0646365 A | 4/1995 |
| EP | 0686379 A2 | 12/1995 |
| EP | 0792627 A3 | 11/1997 |
| EP | 0880948 A1 | 12/1998 |
| EP | 0947179 A2 | 10/1999 |
| FR | 2409747 | 10/1980 |
| FR | 2512678 | 11/1985 |
| FR | 2678508 A1 | 1/1993 |
| FR | 2775182 | 8/1999 |
| GB | 2189150 | 10/1987 |
| WO | WO83/00997 | 3/1983 |
| WO | WO90/04982 | 5/1990 |
| WO | WO92/0004 | 1/1992 |

(List continued on next page.)

*Primary Examiner*—David H. Willse
*Assistant Examiner*—Suzette J. Jackson
(74) *Attorney, Agent, or Firm*—Peter Jon Gluck; Vascular Therapies; Guy L. Cumberbatch (57) ABSTRACT

A vascular graft for a primary vessel adapted to bridge a side branch. The graft is especially useful for providing a support tube for a primary graft in the primary vessel on one side of the side branch. The graft includes first and second tubular sections separated by a gap. A bridging member connects the first and second tubular sections across the gap and may include a relatively rigid strut to prohibit relative axial movement of the two sections. There may be one, two or more bridging members to define one, two or more apertures through which blood can flow from within the graft through to the vessel side branch. The graft may include a flexible, desirably fabric, body supported by a wireform stent that is either self- or balloon-expandable. The graft may be deployed within the abdominal aorta on both sides of the renal arteries and have two apertures for blood to flow from the aorta to the renals. The infra-renal section provides a uniform tubular anchoring surface for a trunk portion of a bifurcated graft used to repair an abdominal aneurysm extending to the iliac arteries.

22 Claims, 4 Drawing Sheets

U.S. PATENT DOCUMENTS

| | | | |
|---|---|---|---|
| 4,820,298 A | 4/1989 | Leveen et al. | |
| 4,878,906 A | 11/1989 | Lindemann et al. | |
| 4,886,062 A | 12/1989 | Wiktor | |
| 4,886,065 A | 12/1989 | Collins, Jr. | |
| 4,913,141 A | 4/1990 | Hillstead | |
| 4,969,458 A | 11/1990 | Wiktor | |
| 4,969,890 A | 11/1990 | Sugita et al. | |
| 4,994,071 A | 2/1991 | MacGregor | |
| 5,019,090 A | 5/1991 | Pinchuk | |
| 5,037,427 A | 8/1991 | Harada et al. | |
| 5,047,050 A | 9/1991 | Arpesani | |
| 5,057,092 A | 10/1991 | Webster, Jr. | |
| 5,064,435 A | 11/1991 | Porter | |
| 5,067,957 A | 11/1991 | Jervis | |
| 5,078,726 A | 1/1992 | Kreamer | |
| 5,078,736 A | 1/1992 | Behl | |
| 5,085,635 A | 2/1992 | Cragg | |
| 5,104,404 A | 4/1992 | Wolff | |
| 5,133,732 A | 7/1992 | Wiktor | |
| 5,183,085 A | 2/1993 | Timmermans | |
| 5,192,297 A | 3/1993 | Hull | |
| 5,201,901 A | 4/1993 | Harada et al. | |
| 5,207,695 A | 5/1993 | Trout, III | |
| 5,236,446 A | 8/1993 | Dumon | |
| 5,275,622 A | 1/1994 | Lazarus et al. | |
| 5,342,387 A | 8/1994 | Summers | |
| 5,354,309 A | 10/1994 | Schnepp-Pesch et al. | |
| 5,360,443 A | 11/1994 | Barone et al. | |
| 5,366,504 A | 11/1994 | Andersen et al. | |
| 5,383,928 A | 1/1995 | Scott et al. | |
| 5,387,235 A | 2/1995 | Chuter | |
| 5,397,345 A | 3/1995 | Lazarus | |
| 5,415,664 A | 5/1995 | Pinchuk | |
| 5,429,144 A | 7/1995 | Wilk | |
| 5,443,496 A | 8/1995 | Schwartz et al. | |
| 5,443,498 A | 8/1995 | Fontaine | |
| 5,456,713 A | 10/1995 | Chuter | |
| 5,464,449 A * | 11/1995 | Ryan et al. | 623/1.35 |
| 5,507,767 A | 4/1996 | Maeda et al. | |
| 5,507,771 A | 4/1996 | Gianturco | |
| 5,522,880 A | 6/1996 | Barone et al. | |
| 5,562,724 A | 10/1996 | Vorwerk et al. | |
| 5,562,727 A | 10/1996 | Turk et al. | |
| 5,562,728 A | 10/1996 | Lazarus et al. | |
| 5,571,170 A | 11/1996 | Palmaz et al. | |
| 5,571,173 A | 11/1996 | Parodi | |
| 5,575,817 A | 11/1996 | Martin | |
| 5,578,071 A | 11/1996 | Parodi | |
| 5,578,072 A | 11/1996 | Barone et al. | |
| 5,591,229 A | 1/1997 | Parodi | |
| 5,609,627 A | 3/1997 | Goicoechea et al. | |
| 5,643,208 A | 7/1997 | Parodi | |
| 5,683,450 A | 11/1997 | Goicoechea et al. | |
| 5,683,451 A | 11/1997 | Lenker et al. | |
| 5,693,086 A | 12/1997 | Goicoechea et al. | |
| 5,693,087 A | 12/1997 | Parodi | |
| 5,709,713 A | 1/1998 | Evans et al. | |
| 5,713,948 A * | 2/1998 | Uflacker | 623/1.35 |
| 5,716,365 A | 2/1998 | Goicoechea et al. | |
| 5,718,724 A | 2/1998 | Goicoechea et al. | |
| 5,752,522 A | 5/1998 | Murphy | |
| 5,769,887 A * | 6/1998 | Brown et al. | 623/1.35 |
| 5,782,904 A | 7/1998 | White et al. | |
| 5,860,923 A | 1/1999 | Lenker et al. | |
| 5,944,750 A | 8/1999 | Tanner et al. | |
| 5,957,940 A | 9/1999 | Tanner et al. | |
| 5,984,955 A * | 11/1999 | Wisselink | 623/1.35 |
| 6,059,824 A * | 5/2000 | Taheri | 623/1.15 |
| 6,102,940 A * | 8/2000 | Robichon et al. | 623/1.35 |
| 6,152,956 A * | 11/2000 | Pierce | 623/1.13 |
| 6,162,246 A * | 12/2000 | Barone | 623/1.35 |

FOREIGN PATENT DOCUMENTS

| | | |
|---|---|---|
| WO | WO95/08966 | 4/1995 |
| WO | WO96/10375 | 4/1996 |
| WO | WO96/28116 | 9/1996 |
| WO | WO98/07389 | 2/1998 |
| WO | WO99/65418 | 12/1999 |

* cited by examiner

VASCULAR GRAFTS FOR BRIDGING A VESSEL SIDE BRANCH

FIELD OF THE INVENTION

The present invention relates to prosthetic vascular grafts and, more particularly, to a vascular graft for a primary vessel adapted to bridge a side branch, especially for providing a support tube for a primary graft located in the primary vessel on one side of the side branch.

BACKGROUND OF THE INVENTION

An aneurysm is a ballooning of the wall of an artery resulting from weakening due to disease or other condition. Left untreated, the aneurysm may rupture, resulting in severe loss of blood and potentially death. An aneurysm in the abdominal aorta is the most common form of arterial aneurysm. The abdominal aorta connects the ascending aorta at the heart to the circulatory system of the trunk and lower body. The abdominal aorta extends downward from the heart in front of and parallel to the spine, through the thorax and abdomen, and branches off in a plurality of side vessels. Among other branching vessels, the abdominal aorta supplies the two kidneys via oppositely-directed renal arteries. Below the renal arteries, the abdominal aorta continues to about the level of the fourth lumbar vertebrae and divides at a Y-junction into the left and right iliac arteries, which supply blood to the lower extremities.

A common location for an aortic aneurysm is in the section of aorta between the renal and iliac arteries. Without rapid surgical intervention, a rupture of the abdominal aorta is commonly fatal because of the high volume of blood flow within the aorta. Conventional surgical intervention involves penetrating the abdominal wall to the location of the aneurysm to reinforce or replace the diseased section of the aorta. Typically, a prosthetic tube graft replaces the area of, or proximal and distal zones abutting, a potential rupture portion of the aorta. Unfortunately, conventional surgical intervention has resulted in substantial morbidity rates, and at the very least a protracted recovery period. Likewise, cost and other constraints militate for a longstanding need for endovascular intervention.

In recent years, methods and devices have been developed to treat an aortic aneurysm without opening up the abdominal wall. These new techniques typically involve a catheter-carried tubular graft delivered upward from the femoral artery through the iliac artery and into the region of the aneurysm. The graft normally includes a tubular graft body supported by an expandable stent, either self-expanding or balloon-expanding. The balloon-expanding type of stent naturally requires an expansion balloon, while the self-expanding type is simply deployed from the end of a tubular sheath. Implacement issues impact upon both known techniques.

If the aneurysm affects the Y-junction between the abdominal aorta and the iliac arteries, a bifurcated graft is typically used. A trunk portion of the bifurcated graft is secured to a healthy section of the abdominal aorta just below the renal arteries, and branched legs of the graft are secured within each of the iliac arteries, sometimes via a tubular extension graft. This procedure does not involve cardiopulmonary bypass, and thus blood continues to flow downward through the abdominal aorta. Certain complications arise in anchoring the graft to the inner wall of the vessel, because of the high blood flow both during the procedure and afterward. Indeed, the risk of grafts migrating within a vessel is a problem in many locations, not just in the abdominal aorta. In addition, the abdominal aorta may be aneurysmic very close to the renal arteries, which results in a fairly poor substrate within which to secure a repair graft. In fact, surgeons require various minimum lengths of healthy aortic wall below the renal arteries before an endovascular graft repair is indicated, or else a conventional invasive technique must be used. Moreover, the same consideration of a minimum healthy portion of the host vessel applies in other areas, especially with regard to the portion of the aorta adjacent the branching subclavian or carotid arteries.

A number of techniques have been proposed for anchoring grafts to vessel walls, most notably the use of barbs or hooks extending outward from graft that embed themselves into the vessel wall. Although these devices secure the graft, they may damage the vessel wall and cause complications. Alternatively, portions of the stent may extend beyond the upstream end of the graft body and be bent outward into contact with the vessel wall, either from a pre- or shape memory-bias, or from expansion of a balloon in this region.

In the context of repairing an aneurysm in the abdominal aorta, some manufacturers have provided a stent at the upper end of a bifurcated graft that extends across the renal arteries. For example, the TALENT brand of Endovascular Stent-Graft System available from World Medical of Sunrise, Florida, includes an undulating wire support frame extending above the graft body intended for supra-renal fixation. Likewise, the ZENITH AAA brand of Endovascular Graft from Cook, Inc. of Bloomington, Indiana, utilizes an undulating wire support having barbs for supra-renal fixation of the graft. However, because these wires extend across the opening of the branching renal arteries they present a certain impediment to blood flow therethrough. Moreover, any structure placed in the path of blood flow may tend to initiate the blood clotting cascade, which in turn, may generate free-floating emboli that would adversely impact the kidneys, or other organ that is perfused through the affected side branch. Because the kidneys are highly susceptible to injury from incursion of such emboli, it is highly desirable to avoid even the possibility of blood clotting at the mouth of the renal arteries.

Despite much work in this highly competitive field, there is still a need for a more secure means of anchoring a bifurcated graft in the abdominal aorta. More generally, there is a need for a more secure means of anchoring a tubular graft in a primary vessel in the vicinity of a vessel side branch.

SUMMARY OF THE INVENTION

The present invention comprises a vascular graft adapted for placement in a primary blood vessel and suited to bridge a vessel side branch. The graft comprises a tubular structure defining an outer surface, a first portion of the outer surface being sized to contact and support the blood vessel on one side of the side branch, and a second portion of the outer surface being sized to contact and support the blood vessel on the other side of the side branch. The tubular structure defines an aperture for alignment with the side branch so as to permit blood flow between the blood vessel and the side branch. The first and second portions may be separated across a gap and the graft further may include at least one bridging member traversing the gap and connecting the first and second portions so as to prevent relative axial separation of the two portions after implantation, the aperture being defined between the bridging member and the first and second portions. There are desirably at least two bridging members and two apertures, and potentially four bridging members and four apertures. Further, the bridging member may be a relatively rigid strut.

In another aspect, the invention provides a vascular graft adapted for placement in a primary blood vessel and suited to bridge a vessel side branch, comprising:

a first tubular structure sized to contact and support the blood vessel on one side of the side branch;

a second tubular structure sized to contact and support the blood vessel on the other side of the side branch; and at least one bridging member connecting the first and second tubular structures so as to define an aperture in the vascular graft sized for blood to flow through between the blood vessel and the side branch.

At least one of the first and second tubular structures desirably comprises a flexible graft body and a support stent, wherein the strut is directly connected to the graft body. More preferably, the flexible graft body is only provided in one of the first or second tubular structures, the other tubular structure being defined solely by the stent.

In a further aspect, the invention provides a vascular graft system adapted for placement in a primary blood vessel and adjacent a vessel side branch. The system includes a tubular support graft including a first tubular structure sized to contact and support the blood vessel on one side of the side branch, and a second tubular structure spaced from and connected to the first tubular structure and sized to contact and support the blood vessel on the other side of the side branch. The system further includes a tubular primary graft sized to co-axially couple with the first tubular structure. At least one bridging member may connect the first and second tubular structures so as to prevent relative axial separation of the two tubular structures after implantation, an aperture being defined between the bridging member and the first and second tubular structures of a sufficient size to permit blood flow though the vessel side branch. In one application of the system, the primary vessel is the abdominal aorta, the vessel side branch comprises the renal arteries, and the tubular primary graft is a portion of a bifurcated graft. In addition, at least one of the first and second tubular structures preferably comprises a flexible graft body and a support stent, and more preferably the flexible graft body is only provided in the tubular structure that is disposed infra-renally, the other tubular structure disposed supra-renally being defined solely by the stent. The stent may be self-expandable or balloon-expandable.

Methods of supporting a tubular primary graft in a primary blood vessel adjacent a vessel side branch is also provide by the present invention. One method includes, providing a tubular support graft including a first tubular section and a second tubular section connected to the first tubular section;

delivering the tubular support graft into an implant position;

deploying the tubular support graft so that the first tubular section contacts and supports the blood vessel on one side of the side branch and the second tubular section contacts and supports the blood vessel on the other side of the side branch;

providing a tubular primary graft having a first end;

delivering the first end of the primary graft within the support graft second tubular section; and radially expanding the first end of the primary graft against the inner surface of the second tubular section.

Another method includes the steps of:

providing a tubular primary graft having a first end;

delivering the first end of the primary graft into an implant position; and radially expanding the first end of the primary graft against the inner surface of the blood vessel on one side of the side branch.

providing a tubular support graft including a first tubular section and a second tubular section connected to the first tubular section;

delivering the tubular support graft so that the second tubular section is within the primary graft first end; and radially expanding the tubular support graft so that the first tubular section contacts and supports the blood vessel on one side of the side branch and the second tubular section contacts and supports the inner surface of the primary graft first end.

Either method is preferably accomplished by endoluminally delivering both the tubular support graft and the tubular primary graft.

A further understanding of the nature and advantages of the invention will become apparent by reference to the remaining portions of the specification and drawings.

DESCRIPTION OF THE PREFERRED EMBODIMENTS

Figure 1:
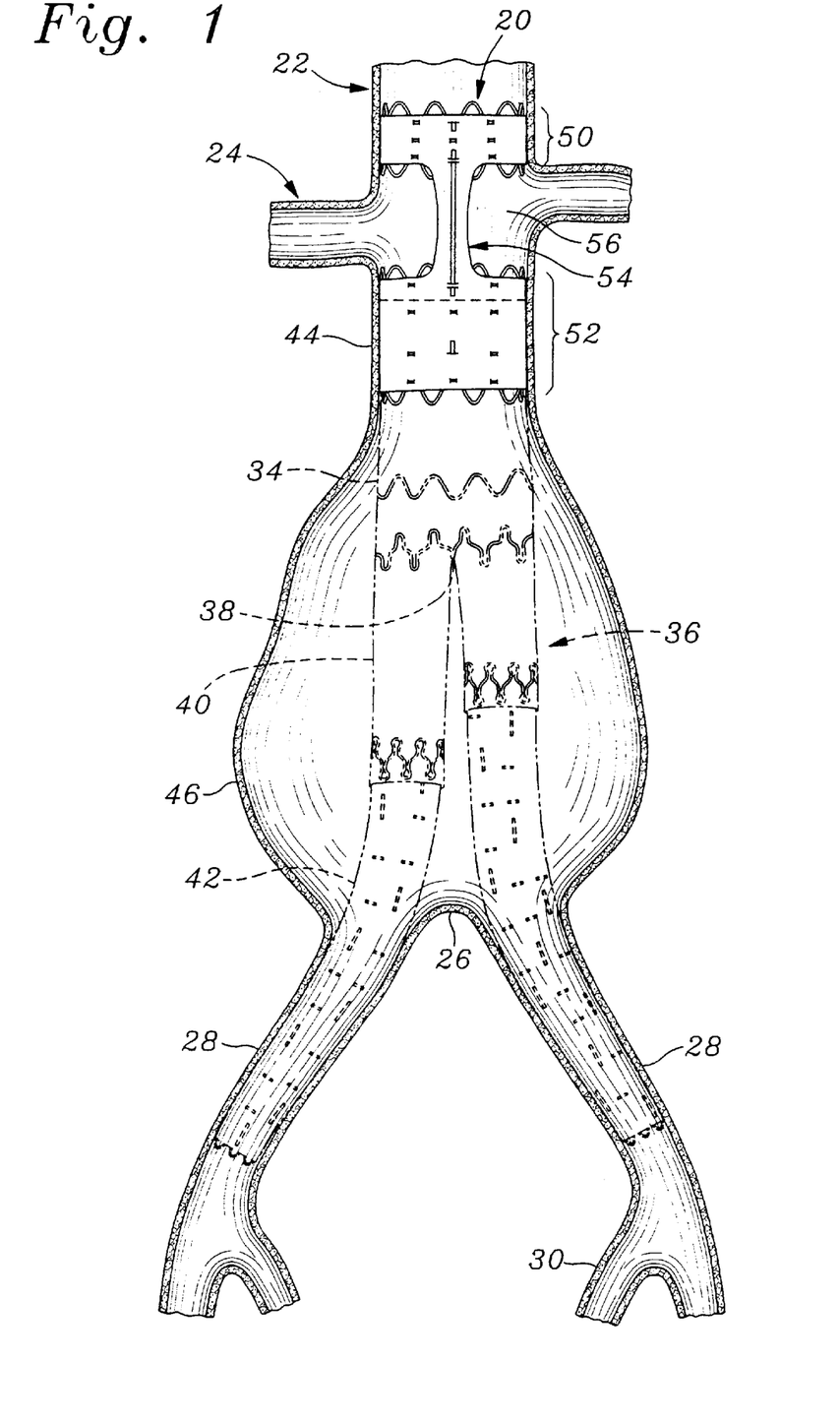
FIG. 1 is a sectional view through an abdominal aorta showing the branching renal and iliac arteries, and illustrating one embodiment of a graft of the present invention for supporting a trunk portion of a bifurcated graft, shown in phantom.

FIG. 1 illustrates a graft 20 of the present invention deployed within a primary vessel, in this case the abdominal aorta 22. A pair of side branches 24 is shown intersecting the primary vessel 22 at approximately the same axial location across the vessel. In the context of an abdominal aorta 22, two important side branches are the renal arteries 24, as shown. The abdominal aorta 22 continues downward from the renal arteries 24 and bifurcates at a Y-junction 26 into the left and right iliac arteries 28.

The present invention provides a tubular graft within a primary vessel for supporting another tubular graft in the primary vessel in proximity to a side vessel. It should therefore be understood that although the drawings and description involve a graft in the abdominal aorta for supporting another graft in the region of the renal arteries, the same principles apply whichever primary vessel or side vessel is involved. For example, as illustrated in FIG. 1, the graft 20 could be used in the vicinity of a side branch 30 in the iliac arteries 28. Representative conditions suitable for repair with the grafts of the present invention include the abdominal aortic aneurysm (AAA) described herein, a thoracic aortic aneurysm (TAA), and an aortic uni-iliac (AUI) aneurysm. For purpose of explanation, however, the term "side branch" will be used interchangeably herein with "renal artery," and the term "primary vessel" will be used interchangeably with "abdominal aorta."

As illustrated in FIG. 1, the graft 20 helps anchor a trunk portion 34 of a bifurcated graft 36, shown in phantom. The bifurcated graft 36 typically comprises the trunk portion 34 that diverges at a septum 38 into a pair of legs 40. One or both of the legs 40 may extend a sufficient distance to form a seal within the iliac arteries 28, or tubular extensions 42 may be provided for this purpose. The end result is that the bifurcated graft 36 (and optional tubular extensions 42) extends from a healthy portion 44 of the abdominal aorta 22 to both of the iliac arteries 28, spanning an aneurysmic region 46. Once the bifurcated graft 36 is in place, blood flows therethrough and blood pressure is reduced between the aneurysm 46 and the exterior of the graft. Ultimately, the aneurysm 46 collapses inward around the graft, which remains in place.

Figure 2:
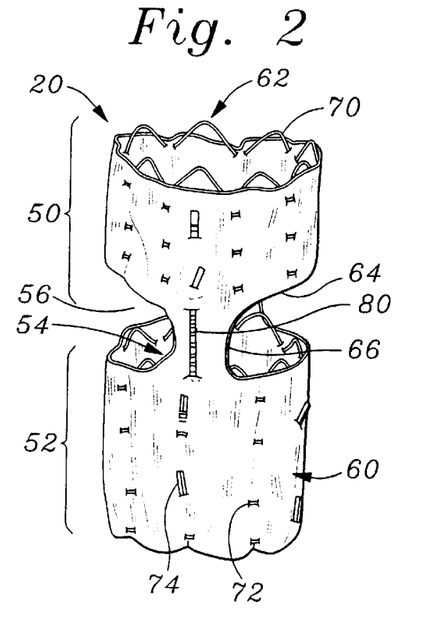
FIG. 2 is a perspective view of the graft of FIG. 1.

With reference to FIGS. 1 and 2, the graft 20 of the present invention comprises a first tubular section 50 and a second tubular section 52 connected via at least one bridging member 54. The first tubular section 50 is spaced from the second tubular section 52 across a gap that, in conjunction with the bridging member 54, defines an aperture 56 for blood flow. If the first and second tubular sections 50, 52 are co-linear, then the bridging member 54 is generally axially disposed. Alternatively, if the graft 20 is intended for implantation in a curvilinear vessel, the first and second tubular sections 50, 52 may be aligned along a curvilinear axis, in which case the bridging member 54 will also be generally disposed along the same curve. Still further, the graft 20 may be multi-curvate, for example S-shaped, in which case the first and second tubular sections 50, 52 and bridging member 54 will follow the multiple curves.

As illustrated in FIG. 1, the aperture 56 is aligned with at least one of the side branches 24. In a preferred application, the graft 20 is used to support a bifurcated graft 36 in proximity with the renal arteries 24, and thus defines two apertures 56, each aligned with one of the renal arteries. In this context, the first tubular section 50 is secured in contact with a supra-renal portion of the abdominal aorta 22, while the second tubular section 52 is secured in contact with an infra-renal portion. The apertures 56 are sized large enough so that no portion of the graft 20 resides in the blood flow path of the renal arteries 24, and also so that renal arteries that are slightly axially offset from one another can be accommodated.

With specific reference to FIG. 2, the graft 20 comprises a tubular graft body 60 internally supported by a stent 62. The tubular graft body 60 may be formed of one or more pieces, typically of a biocompatible fabric such as polyester (e.g., polyterepthalate). Alternatively, the graft body 60 may be an extruded PTFE tube. In a particular preferred embodiment, the graft body 60 is one piece, with the apertures 56 formed by diametrically-opposed, generally oval-shaped windows 64 cut in the body and extending circumferentially around the body into proximity with one another. Two bridge segments 66 of the graft body 60 extend between the first and second tubular sections 50, 52 of the graft and separate the windows 64. Preferably, the bridge segments 66 extend circumferentially around the graft body 60 a small arc in relation to the adjacent windows 64 so as to maximize the size of the blood flow apertures 56. In one embodiment, the bridge segments 66 each circumferentially extends between about 1–90° around the graft body 60, and more preferably each extends about 5–10°.

The blood flow apertures 56 are sized to enable alignment with side branches of varying sizes. Of course, the particular size is defined by the axial dimension and the circumferential arc of the windows 64, which depends on the overall graft diameter and length. For instance, a graft that is designed for small arteries and small side branches will have a reduced diameter and reduced window size. Additionally, if the graft is intended to bridge only one side branch then only one window is required. In a preferred embodiment, for use in the abdominal aorta 22 to bridge the renal arteries 24, the graft 20 has a diameter of between about 19 and 30 mm, and a length of between about 22 and 46 mm. The opposed windows 64 have an axial length of between about 6 and 20 mm, and extend circumferentially around the graft body 60 between about 90° and 189°. The renal arteries 24 typically have a diameter of between about 8–10 mm, and thus the windows 64 are desirably oversized to ensure open blood flow through the renals, and to accommodate offset or otherwise misaligned pairs of renals.

The stent 62 actually comprises a first stent portion within the first tubular section 50, and a second stent portion within the second tubular section 52. The first and second stent portions may be substantially similar in construction, or may be configured differently, as desired. Those of skill in the art will understand that a variety of different types of stents may be used to internally support a tubular graft body.

In a preferred embodiment, the stent 62 comprises a plurality of separate, spaced-apart wireforms 70, each formed in an undulating, or sinusoidal pattern. Each of the wireforms 70 includes alternating peaks and valleys, with either the peaks or valleys being woven through the graft body. More specifically, as seen in FIG. 2, there are three axially-spaced rows of wireforms 70 in the first tubular section 50, and four axially-spaced rows of wireforms in the second tubular section 52. Either the peaks or valleys of these rows of undulating wireforms are woven through slits 72 formed in the graft body 60. In this manner, the wireforms 70 are prevented from migrating axially within the graft body 60 with respect to one another, and thus provide a fairly uniform inner support structure for the flexible graft body. As mentioned, each wireform is either radially self-expandable to the configuration shown, or is capable of plastic deformation when balloon-expanded. In either case, the stent 62 (comprising the array of wireforms 70) compresses the graft body 62 against the inner wall of a tubular blood vessel to form a fluid seal therebetween. Moreover, certain materials and/or sleeve-like structures are available to enhance the seal between the exterior of the graft 20 and the vessel wall, and may be combined with the present invention.

A plurality of crimps 74 is visible on the exterior of the graft body 62. The crimps 74 join free ends of each wireform 70, which comprise one or more wire segments bent into the undulating pattern, and into the annular shape required. Though the crimps 74 are not sharp, they provide an irregular surface structure on the exterior of the graft 20, and thus help secure the graft in position within the vessel.

The bridging member 54 seen in FIGS. 1 and 2 comprises a reinforcing strut 80 and the aforementioned bridge segments 66 of the graft body 60. The reinforcing strut 80 is a relatively rigid elongate member extending between the first and second tubular sections 50, 52 of the graft 20. In a preferred embodiment, the reinforcing strut 80 is a biocompatible metal (e.g., stainless-steel) strip or rod secured at each end to either the graft body 60 or the stent 62. If the ends of the reinforcing strut 80 are secured to the graft body 60 as shown, sutures are typically used to sew an eyelet, hook or other such feature (not shown) provided on each end of the reinforcing strut. If the ends of the reinforcing strut 80 are secured to the stent 62, crimps are preferably used between juxtaposed ends of the closest wireforms and the reinforcing strut. As shown, the reinforcing struts 80 are desirably located to the outside of the bridge segments 66, although the reverse configuration is contemplated as well.

The bridging members 54 serve to anchor one of the first and second tubular sections 50, 52 of the graft 20 with respect to the other, and desirably maintain the spacing between the tubular sections, while at the same time present very little in the way of structure that might occlude or otherwise interfere with the blood flow between the primary vessel 22 and the affected side branch 24. The bridging members 54 must have tensile strength to withstand migratory forces that may tend to separate the first and second tubular sections 50, 52. In an exemplary configuration, the upstream section 50 or 52 serves to anchor the downstream section by virtue of their connection with the bridging members 54. In addition, the bridging members 54 may be relatively rigid in the sense that they have column strength sufficient to prevent the tubular sections 50, 52 from migrating toward each other after implantation.

The bridging members 54 have a radial dimension that is approximately the same as the rest of the graft 20; that is, they do not project radially into or out from the side wall of the graft. The circumferential width of each bridging member 54 depends on the intended use for the graft 20. That is, if the graft 20 is to be used in the abdominal aorta 22 to bridge the renal arteries 24 as shown in the drawings, then there are two bridging members 54 diametrically spaced apart of relatively narrow circumferential width. In this way, the bridging members 54 each axially extend along the wall of the abdominal aorta 22 at 90° orientations from the openings to the renal arteries 24, and there is no chance of occluding blood flow between the abdominal aorta 22 and renal arteries 24. Alternatively, if there is only one side branch then there need only be one bridging member of relatively greater circumferential width than as shown. That is, the bridging member might extend 180° or more around the graft, with the corresponding window opening up the remaining portion. In general, as long as care is taken to orient the window(s) in registration with the side branch or branches, then the bridging member(s) will not occlude blood flow.

The embodiment of FIGS. 1 and 2 shows relatively rigid bridging members 54 that are constructed of, for example, wires. Alternatively, the bridging members 54 may be strips of biocompatible fabric or even sutures that provide tensile strength to prevent the downstream tubular section 52 from migrating with respect to the upstream section 50. In the illustrated example, the upstream section 50 anchors the graft 20, and in particular the downstream tubular section 52, with respect to the renal arteries 24. In this context, one or the other of the tubular sections 50, 52 may be designed to better anchor the graft 20 in the primary artery 22, and the other may perform another function, such as supplementing a damaged section of the artery so that another graft may be secured adjacent the side branch 24. Of course, however, both tubular sections 50, 52 can be constructed to have identical anchoring and vessel supporting characteristics if the graft 20 is used to repair a damaged length of the vessel that extends upstream and downstream of the side branch.

Figure 3:
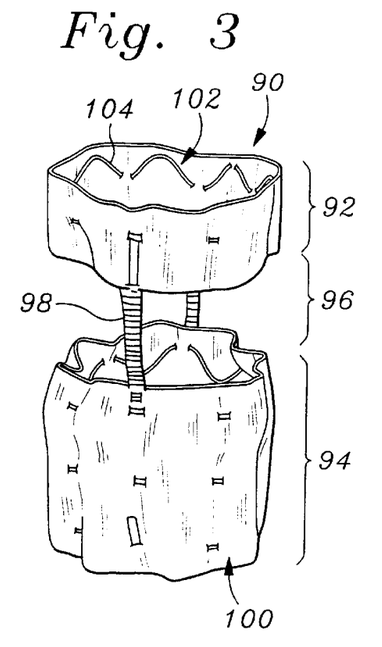
FIG. 3 is a perspective view of an alternative graft in accordance with the present invention having two planar bridging members.

FIG. 3 illustrates an alternative graft 90 of the present invention having a first tubular section 92 separated from a second tubular section 94 across a gap 96 and connected across the gap by two bridging members 98. Again, the graft 90 comprises a graft body 100 and an internal stent 102. The graft body 100 may be a tubular biocompatible fabric, and in the illustrated embodiment is separated across the gap 96 into two tubular portions in the respective first and second tubular sections 92, 94. Because the facing edges of the two tubular portions of the graft body 100 are circular, the gap 96 is tubular. The stent 102 again comprises a plurality of spaced-apart annular wireforms, although it should be noted that the first tubular section 92 only has a single wireform 104.

The bridging members 98 are elongated planar bars or strips of relatively rigid material, such as stainless-steel or a suitable polymer connected directly to the stent 102 or to the graft body 100 in the first and second tubular sections 92, 94. Again, the bridging members 98 must have must have tensile strength to withstand migratory forces that may tend to separate the first and second tubular sections 92, 94 after implantation, while at the same time must not occlude or otherwise interfere with the blood flow between the primary vessel and the affected side branch or branches. Therefore, instead of being relatively rigid, the bridging members 98 may be strips of fabric, such as polyester, or sutures for that matter.

Figure 4:
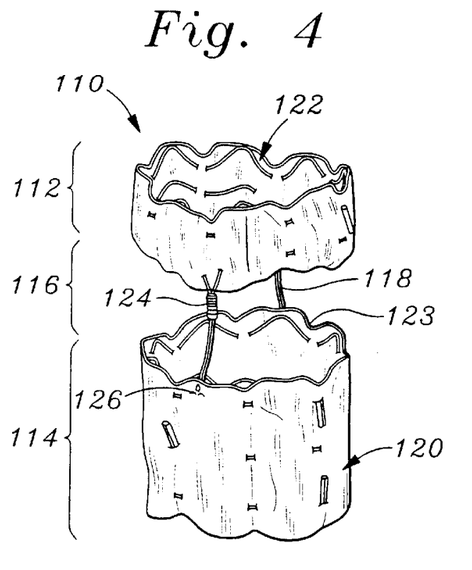
FIG. 4 is a perspective view of a further graft of the present invention having two wire-like bridging members.

FIG. 4 illustrates an alternative graft 110 of the present invention having a first tubular section 112 separated from a second tubular section 114 across a gap 116 and connected across the gap by two bridging members 118. Again, the graft 110 comprises a graft body 120 and an internal stent 122. The graft body 120 may be a tubular biocompatible fabric, and in the illustrated embodiment is separated across the gap 116 into two tubular portions in the respective first and second tubular sections 112, 114. In this case the facing edges of the two tubular portions of the graft body 120 are uneven by virtue of a plurality of notches 123, and thus the gap 116 is uneven as well. The stent 122 again comprises a plurality of spaced-apart annular wireforms, with the first tubular section 112 having two wireforms and the second tubular section 114 having three.

The bridging members 118 each comprises lengths of wire either separate from the stent 122 or defined by extensions of one or the wireforms. If the bridging members 118 are separate from the stent 122, they are connected directly to the stent using a crimp 124, for example, or are connected indirectly via stitching 126 to the graft body 120. In an exemplary embodiment as illustrated, the bridging members 118 are connected via crimps 124 to free ends of the lowest wireform in the first tubular section 112 and sewn to the graft body 120 in the second tubular section 114.

Figure 5:
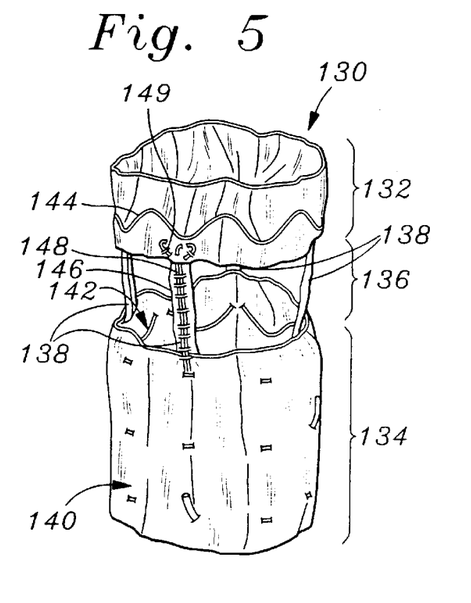
FIG. 5 is a perspective view of a further graft of the present invention having four bridging members.

FIG. 5 illustrates a still further exemplary graft 130 of the present invention having a first tubular section 132 separated from a second tubular section 134 across a gap 136 and connected across the gap by four (4) bridging members 138. Again, the graft 130 comprises a graft body 140 and a stent 142. The graft body 140 is desirably a tubular biocompatible fabric. The stent 142 again comprises a plurality of spaced-apart annular wireforms, with the first tubular section 132 having a single wireform 144 disposed on the exterior of the graft body 140. The external wireform 144 can either be woven through slits in the graft body 140 as described above, or may be secured thereto with the use of suture thread.

The four bridging members 138 are distributed generally equidistantly around the circumference of the graft 130 and each comprises a narrow strip of fabric 146 and a reinforcement strut 148. Again, the reinforcement struts 148 may be connected directly to the stent 142 using a crimp, for example, or are connected indirectly via stitching 149 to the graft body 140. The use of four bridging members 138 may be desirable for stability when smaller branching vessels are involved so that the windows defined between the bridging members need not be as large as the previous embodiments.

Figure 6:
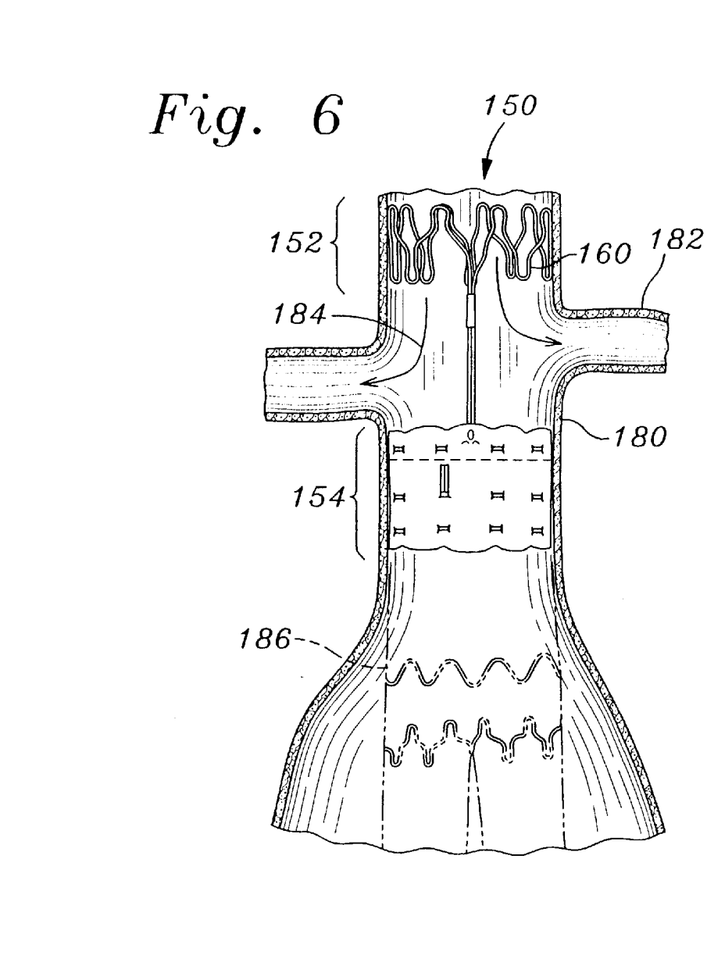
FIG. 6 is a sectional view of the abdominal aorta in the region of the renal arteries illustrating a still further embodiment of a graft of present invention used to support the trunk portion of a bifurcated graft, shown in phantom.
Figure 7:
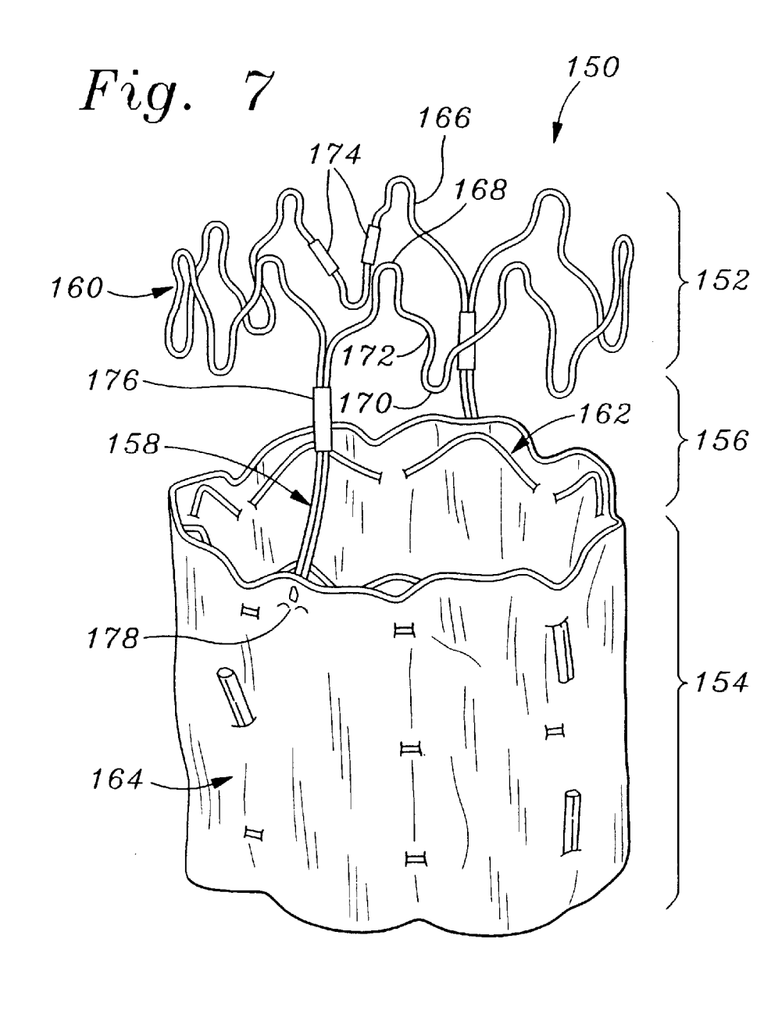
FIG. 7 is a perspective view of the graft of FIG. 6.

FIGS. 6 and 7 illustrate a still further embodiment of a graft 150 of the present invention that defines a tubular structure having a first portion 152 and a second portion 154 separated from the first portion across a gap 156. Two bridging members 158 extend generally axially between and couple the first and second portions 152, 154 to prevent their relative movement before during and after implantation. In this embodiment, the first portion 152 of the tubular structure is defined solely by a stent 160, while the second portion 154 is defined by a stent 162 internally supporting a tubular graft body 164.

The upper stent 160 comprises an annular wireform 166 having alternating peaks 168 and valleys 170 and contoured curvilinear segments 172 extending therebetween. The curvilinear segments 172 are shaped so as to nest together when the graft 150 is in a radially constricted state, so as to enable smaller compaction of the graft. The wireform 166 includes one or more segments connected into the annular shape by one or more crimps 174. The lower stent 162 includes a plurality of axially-spaced undulating wireforms woven through the graft body 164, as previously described.

The bridging members 158 each comprise lengths of wire either separate from the stents 160, 162 or defined by extensions of one or the wireforms. If the bridging members 158 are separate from the stents 160, 162, they are connected directly to the upper stent 160 using a crimp 176, and are connected directly to the lower stent 162 using a crimp or indirectly via stitching 178 to the graft body 164. In an exemplary embodiment as illustrated, the bridging members 158 are connected via crimps 176 to free ends of the wireform 166 in the first portion 152 and sewn to the graft body 164 in the second portion 154.

FIG. 6 shows the graft 150 in place within a primary vessel 180 (e.g., the abdominal aorta) and bridging two oppositely-directed vessel side branches 182 (e.g., the renal arteries). The first portion 152 is located to contact and support the primary vessel 180 on one side of the side branches 182, while the second portion 154 is located to contact and support the primary vessel on the other side of the side branches. The gap 156 is positioned to permit blood flow between the primary vessel 180 and side branches 182, as indicated by the flow arrows 184. The bridging members 158 extend axially across the gap 156 against the wall of the primary vessel 180 at approximately 90° orientations from the side branches 182. Another graft 186 (e.g., the trunk of a bifurcated graft) is seen positioned within the second portion 154. In this way, the graft 186 is secured within the uniform and tubular second portion 154, which in turn is anchored within the primary vessel 180 from its own contact with the vessel wall, and by virtue of its connection to the first portion 152 via the bridging members 158. This system of supporting one graft with another permits graft positioning very close to the vessel side branches 182, and is especially effective when the primary vessel is distended even very close to the side branches.

The axial dimensions of the various grafts disclosed herein may be selected to match the particular anatomical dimensions surrounding the affected side branch. That is, the grafts, including two tubular sections with an aperture or gap therebetween and bridging members connecting the sections, are sized so as to permit blood flow through the affected side branch and any adjacent side branches. For example, the graft 150 seen in FIGS. 6 and 7 is positioned so that the first portion 152 is above the renal arteries 182 and the second portion 154 is below the renals.

Figure 8:
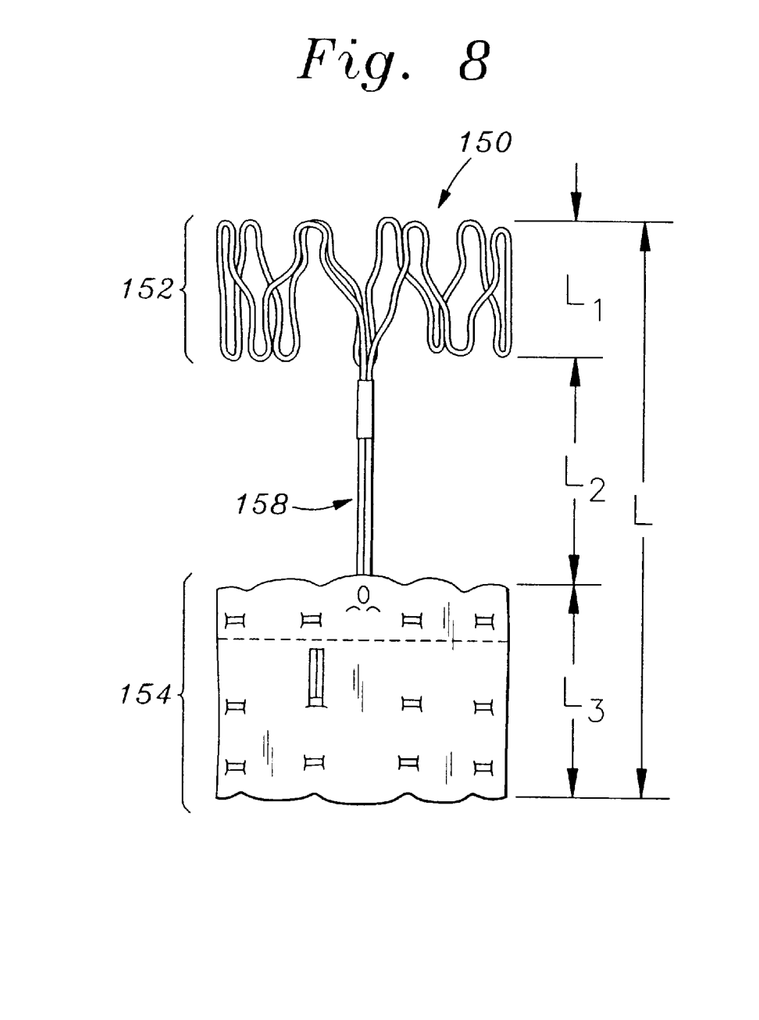
FIG. 8 is an elevational view of the graft of FIG. 6 showing certain axial dimensions.
Figure 9:
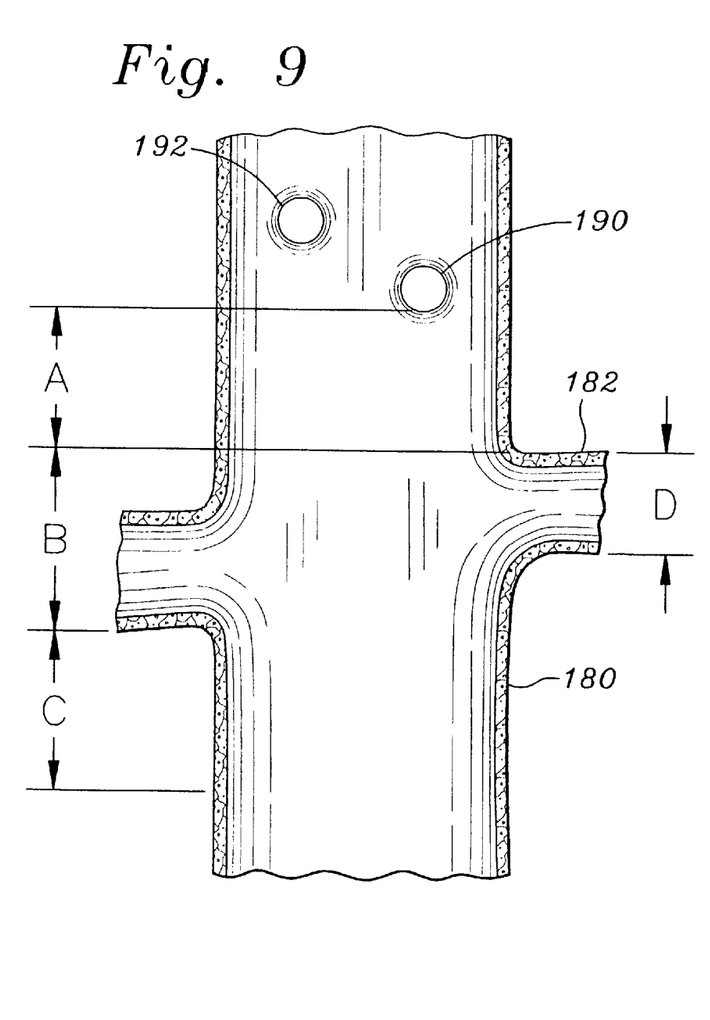
FIG. 9 is an axial sectional view of an abdominal aorta in the region of the renal arteries showing certain anatomical dimensions.

A more detailed depiction of the relative axial dimensions for the graft 150 and region of the abdominal artery 180 near the renals 182 is seen in FIGS. 8 and 9. In addition to the renal arteries 182, the openings for the superior mezzanteric artery 190 and the ciliac artery 192 are shown in FIG. 9. These arteries typically project in the posterior direction, in contrast to the laterally-directed renals 182, and are located close to but upstream of the renals. The distance from the lowest of the arteries 190 or 192 and the highest of the renals 182 is given as A, the distance from the upstream side of the highest of the renals 182 to the downstream side of the lowest of the renals is given as B, and the distance between the downstream side of the lowest of the renals to the end of the perceived healthy portion of the abdominal aorta 180 is given as C. In addition, the diameter of one of the renal arteries 182 is given as D. The axial dimensions of the graft 150 are given in FIG. 8 as: L for the overall for the tubular structure, $L_1$ for the first portion 152, $L_2$ for the gap 156, and $L_3$ for the second portion 154.

In a preferred embodiment, $L_2 > D$, and if the renal arteries 182 are offset, $L_2 > B$. In addition, $L_1$ is preferably smaller than or equal to A, so that the first portion 152 does not occlude either of the arteries 190 or 192. Finally, the length $L_3$ of the second portion 154 is desirably less than the length C of the healthy portion of the abdominal aorta 180, but may be greater than C.

In a specific embodiment, for use in the abdominal aorta 180 to bridge the renal arteries 182, the graft 150 has a diameter of between about 19 and 30 mm, and a length L of between about 22 and 46 mm. The renal arteries 182 typically have a diameter of between about 5–10 mm, and may be offset center-to-center up to 10 cm. Thus the gap 156 has an axial length $L_2$ of between about 6 and 20 mm, and is desirably oversized to ensure open blood flow through the renals and to accommodate offset or otherwise misaligned pairs of renals. The length $L_1$ for the first portion 152 is desirably about 6 mm, but may vary depending on need. The length C of the healthy portion of the abdominal aorta 180 should be at least 5 mm to enable the proper seal of the second portion 154 with the aorta, which is smaller than an endovascular repair would currently be indicated. The length $L_3$ of the second portion 154 is preferably at least 6 mm, more preferably about 10–20 mm. Of course, if the graft 20 is used to repair a longer section of vessel as a primary graft, the length $L_3$ of the second portion 154 can be longer than 20 mm, up to the currently accepted maximum length of straight tube vascular graft.

To ensure the proper size/configuration of graft, the surgeon first determines the anatomical landscape through the use of angioscopy; that is, by injecting a contrast media and visualizing flow through the affected vessels with an X-ray device. The dimensions noted in FIG. 9 can thus be obtained. A range of different sized grafts are preferably available, and the surgeon then selects the graft to match the anatomy in conformance with the above preferred guidelines.

During implantation, the surgeon can ensure proper placement and orientation of the grafts of the present invention with the use of radiopaque markers on the graft. For example, the stent structure, or portions thereof, could be radiopaque, or markers can be attached to the stent or graft body. In FIG. 7, for instance, the wireform 160 and the upper wireform in the stent 162 are desirably radiopaque so as to enable the surgeon to monitor the approximate axial borders of the gap 156. Furthermore, the bridging members 158 or crimps 176 may be radiopaque to enable rotational orientation with respect to the respective side branch or branches.

A method of supporting a tubular primary graft in a primary blood vessel adjacent a vessel side branch, in accordance with the present invention can be illustrated with reference to the embodiment of FIG. 6. First, the tubular graft 150 is implanted in the primary vessel 180 such that the first portion 160 contacts and supports the primary vessel on one side of a side branch 182, in this case the two renal arteries, and the second portion 154 contacts and supports the primary vessel on the other side of the side branch. Implantation of the tubular graft 150 can be accomplished by releasing a self-expandable version of the graft from within a catheter sheath in the proper location, or positioning a balloon-expandable version of the graft and inflating a balloon within the interior of the graft. A primary graft 186 is then delivered in a radially constricted state to a position overlapping the end of the second portion 154 and radially expanded into contact therewith. Again, the primary graft 186 may be either self-expanding or balloon-expanding.

An alternative method comprises implanting the tubular graft 150 after the implantation of the primary graft 186. That is, the second portion 154 of the tubular graft 150 is self- or balloon- expanded outward into contact with the primary graft 186. Indeed, the primary graft 186 may be implanted for a significant period of time before the need for the supporting function of the tubular graft 150 is recognized.

As mentioned above, one tubular portion of the graft may perform an anchoring s function to maintain the position of the other portion that may or may not have the same anchoring characteristics. For instance, the graft portion upstream of the side branch may anchor the downstream portion, which in turn reinforces, supplements or seals with the primary vessel so as to enable placement of another graft in that location. The present invention has been described so far in terms of self- or balloon-expandable stents for anchoring, but those of skill in the art will recognize that there are other ways to anchor. For instance, staples, bent or corkscrew, are becoming more sophisticated and effective, and may be used for anchoring. For that matter, any means for anchoring one portion of the graft can be used.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A vascular graft adapted for placement in a primary blood vessel and suited to bridge a vessel side branch, comprising:

a tubular structure defining an outer surface, a first portion of the outer surface being sized to contact and support the blood vessel on one side of the side branch, and a second portion of the outer surface being sized to contact and support the blood vessel on the other side of the side branch, the tubular structure defining an aperture for alignment with the side branch so as to permit blood flow between the blood vessel and the side branch;

wherein the first and second portions are separated across a gap and further including at least one bridging member traversing the gap and connecting the first and second portions so as to prevent relative axial separation of the two portions after implantation, the aperture being defined between the bridging member and the first and second portions.

2. The vascular graft of claim 1, including at least two bridging members and two apertures.

3. The vascular graft of claim 1, including four bridging members and four apertures.

4. The vascular graft of claim 1, wherein the bridging member includes a relatively rigid strut.

5. The vascular graft of claim 4, wherein the tubular structure comprises a flexible graft body and a support stent, wherein the strut is directly connected to the stent.

6. The vascular graft of claim 4, wherein the tubular structure comprises a flexible graft body and a support stent, wherein the strut is directly connected to the graft body.

7. A vascular graft adapted for placement in a primary blood vessel and suited to bridge a vessel side branch, comprising:

a tubular structure defining an outer surface, a first portion of the outer surface being sized to contact and support the blood vessel on one side of the side branch, and a second portion of the outer surface being sized to contact and support the blood vessel on the other side of the side branch, the tubular structure defining an aperture for alignment with the side branch so as to permit blood flow between the blood vessel and the side branch;

wherein the tubular structure comprises a flexible graft body and a support stent, and wherein the flexible graft body is only provided in one of the first or second portions, the other portion being defined solely by the stent.

8. A vascular graft adapted for placement in a primary blood vessel and suited to bridge a vessel side branch, comprising:

a first tubular structure sized to contact and support the blood vessel on one side of the side branch;

a second tubular structure sized to contact and support the blood vessel on the other side of the side branch; and four bridging members connecting the first and second tubular structures so as to define four apertures in the vascular graft sized for blood to flow through between the blood vessel and the side branch.

9. The vascular graft of claim 8 wherein the bridging member includes a relatively rigid strut.

10. The vascular graft of claim 9, wherein at least one of the first and second tubular structures comprises a flexible graft body and a support stent, wherein the strut is directly connected to the stent.

11. The vascular graft of claim 9, wherein at least one of the first and second tubular structures comprises a flexible graft body and a support stent, wherein the strut is directly connected to the graft body.

12. A vascular graft adapted for placement in a primary blood vessel and suited to bridge a vessel side branch, comprising:

a first tubular structure sized to contact and support the blood vessel on one side of the side branch;

a second tubular structure sized to contact and support the blood vessel on the other side of the side branch; and at least one bridging member connecting the first and second tubular structures so as to define an aperture in the vascular graft sized for blood to flow through between the blood vessel and the side branch, wherein at least one of the first and second tubular structures comprises a flexible graft body and a support stent, and wherein the flexible graft body is only provided in one of the first or second tubular structures, the other tubular structure being defined solely by the stent.

13. A vascular graft system adapted for placement in a primary blood vessel and adjacent a vessel side branch, comprising:

a tubular support graft including a first tubular structure sized to contact and support the blood vessel on one side of the side branch, and a second tubular structure spaced from and connected to the first tubular structure and sized to contact and support the blood vessel on the other side of the side branch;

a tubular primary graft sized to co-axially couple with the first tubular structure; and at least two bridging members connecting the first and second tubular structures so as to prevent relative axial separation of the two tubular structures after implantation, two apertures being defined between the bridging member and the first and second tubular structures of a sufficient size to permit blood flow though the vessel side branch.

14. The system of claim 13, wherein the primary vessel is the abdominal aorta, the vessel side branch comprises the renal arteries, and the tubular primary graft is a portion of a bifurcated graft.

15. A vascular graft system adapted for placement in a primary blood vessel and adjacent a vessel side branch, comprising:

a tubular support graft including a first tubular structure sized to contact and support the blood vessel on one side of the side branch, and a second tubular structure spaced from and connected to the first tubular structure and sized to contact and support the blood vessel on the other side of the side branch;

a tubular primary graft sized to co-axially couple with the first tubular structure; and four bridging members connecting the first and second tubular structures so as to prevent relative axial separation of the two tubular structures after implantation, four apertures being defined between the bridging member and the first and second tubular structures of a sufficient size to permit blood flow though the vessel side branch.

16. A vascular graft system adapted for placement in a primary blood vessel and adjacent a vessel side branch, comprising:

a tubular support graft including a first tubular structure sized to contact and support the blood vessel on one side of the side branch, and a second tubular structure spaced from and connected to the first tubular structure and sized to contact and support the blood vessel on the other side of the side branch; and a tubular primary graft sized to co-axially couple with the first tubular structure; and at least one relatively rigid strut connecting the first and second tubular structures so as to prevent relative axial separation of the two tubular structures after implantation, an aperture being defined between the strut and the first and second tubular structures of a sufficient size to permit blood flow though the vessel side branch.

17. The system of claim 16, wherein at least one of the first and second tubular structures comprises a flexible graft body and a support stent, wherein the strut is directly connected to the stent.

18. The system of claim 16, wherein at least one of the first and second tubular structures comprises a flexible graft body and a support stent, wherein the strut is directly connected to the graft body.

19. A vascular graft system adapted for placement in the abdominal aorta and adjacent the renal arteries, comprising:

a tubular support graft including a first tubular structure sized to contact and support the abdominal aorta on one side of the renal arteries, and a second tubular structure spaced from and connected to the first tubular structure and sized to contact and support the abdominal aorta on the other side of the renal arteries; and a tubular primary graft sized to co-axially couple with the first tubular structure wherein at least one of the first and second tubular structures comprises a flexible graft body and a support stent, and wherein the stent internally supports the one of the first and second tubular structures that is disposed infra-renally.

20. The system of claim 19, wherein the flexible graft body is only provided in the one of the first and second tubular structures that is disposed infra-renally, the other tubular structure disposed supra-renally being defined solely by the stent.

21. The system of claim 19, wherein the stent is self-expandable.

22. The system of claim 19, wherein the stent is balloon-expandable.

* * * * *